(12) United States Patent
Selve

(10) Patent No.: US 6,803,481 B2
(45) Date of Patent: Oct. 12, 2004

(54) USE OF PEPTIDE CLASS OF COMPOUND FOR TREATING NON NEUROPATHIC INFLAMMATORY PAIN

(75) Inventor: Norma Selve, Troisdorf (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 10/344,885

(22) PCT Filed: Mar. 19, 2002

(86) PCT No.: PCT/EP02/03034

§ 371 (c)(1),
(2), (4) Date: Feb. 11, 2003

(87) PCT Pub. No.: WO02/074784

PCT Pub. Date: Sep. 26, 2002

(65) Prior Publication Data

US 2003/0171300 A1 Sep. 11, 2003

(30) Foreign Application Priority Data

Mar. 20, 2001 (EP) .............................. 01106891

(51) Int. Cl.$^7$ ............................ C07C 261/00
(52) U.S. Cl. ....................... 560/157; 514/616; 514/315; 654/158
(58) Field of Search .................. 560/157; 654/158; 514/616, 315; 564/155, 158

(56) References Cited

U.S. PATENT DOCUMENTS

| 5,378,729 A | * | 1/1995 | Kohn et al. .............. 514/231.2 |
| 5,654,301 A | * | 8/1997 | Kohn et al. .............. 514/231.2 |
| 5,773,475 A | * | 6/1998 | Kohn ........................ 514/616 |

\* cited by examiner

*Primary Examiner*—Paul Killos
*Assistant Examiner*—Hector M. Reyes
(74) *Attorney, Agent, or Firm*—Edwards & Angell, LLP; Jeffrey D. Hsi; Peter F. Corless

(57) ABSTRACT

The present invention concerns the use of compounds of the Formula (I) for treating different types and symptoms of acute and chronic pain, especially non neuropathic inflammatory pain in mammals. The pain to be treated may be e.g. chronic inflammatory pain, rheumatoid arthritis pain and/or secondary inflammatory osteoarthritic pain. The compounds show an antinociceptive profile and differ from classical analgesics like opioids and non-steroidal anti-inflammatory drugs (NSAIDS) and are useful as specific analgesics.

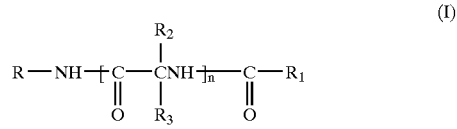

37 Claims, 1 Drawing Sheet

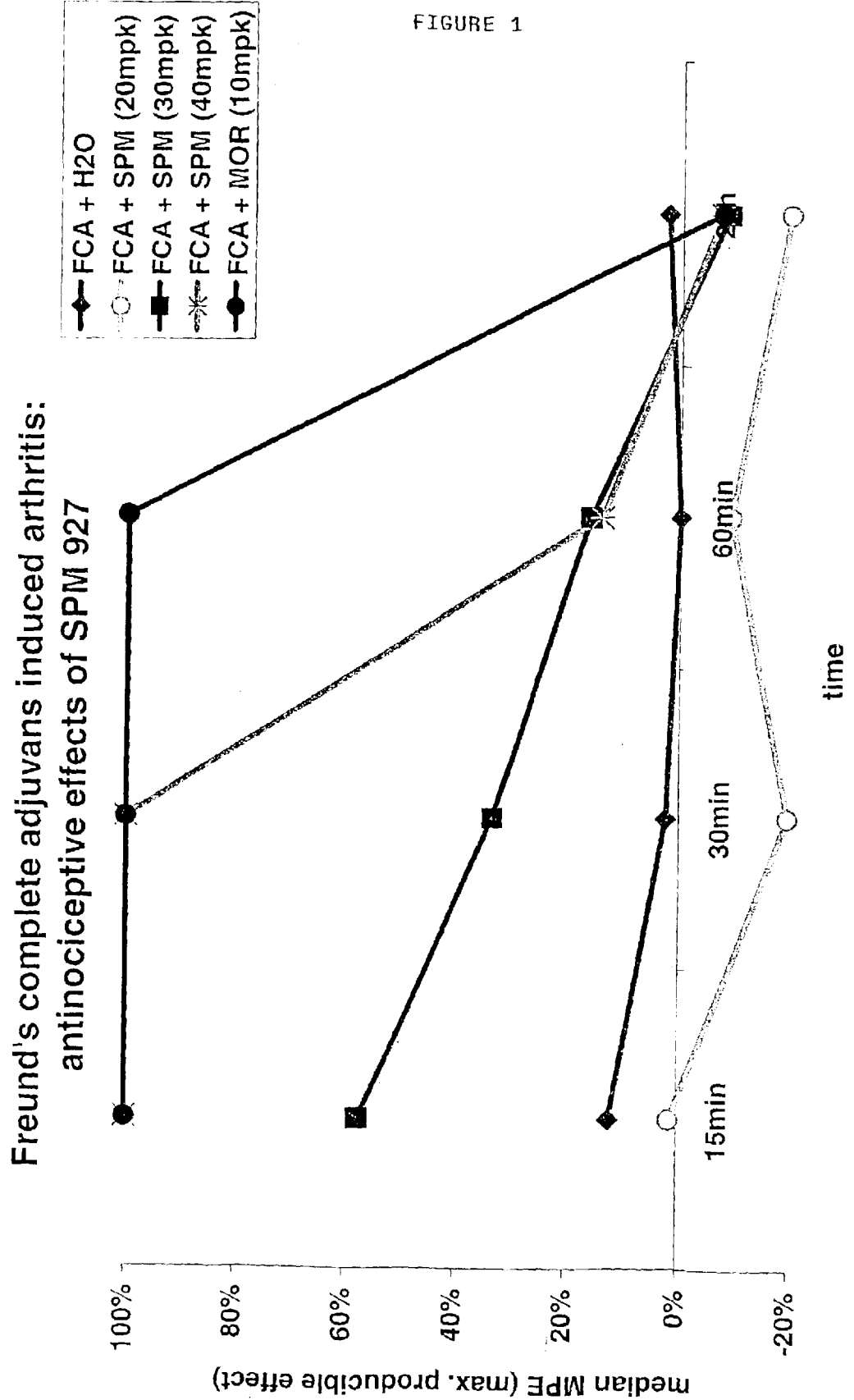

USE OF PEPTIDE CLASS OF COMPOUND FOR TREATING NON NEUROPATHIC INFLAMMATORY PAIN

FIELD OF THE INVENTION

The present invention is directed to the novel use of a peptide class of compound for treating different types and symptoms of acute and chronic pain, especially non neurophathic inflammatory pain.

BACKGROUND OF THE INVENTION

Certain peptides are known to exhibit central nervous system (CNS) activity and are useful in the treatment of epilepsy and other CNS disorders. These peptides which are described in the U.S. Pat. No. 5,378,729 have the Formula (I):

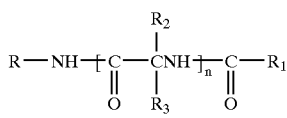

Formula (I)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, $S(O)_2$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_5R_6$ or $PR_4NR_5R_7$,

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and $R_7$ is $R_6$ or $COOR_8$ or $COR_8$;

$R_8$ is hydrogen or lower alkyl, or aryl lower alkyl, and the aryl or alkyl group may be unsubstituted or substituted with an electron withdrawing group or an electron donating group; and n is 1–4; and a is 1–3.

U.S. Pat. No. 5,773,475 also discloses additional compounds useful for treating CNS disorders. These compounds are N-benzyl-2-amino-3-methoxy-propionamide having the Formula (II):

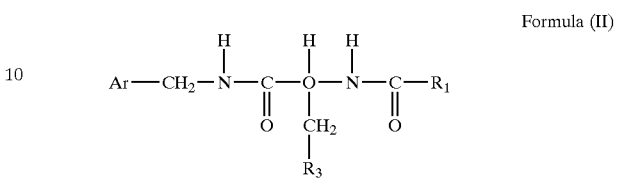

Formula (II)

wherein

Ar is aryl which is unsubstituted or substituted with halo; $R_3$ is lower alkoxy; and $R_1$ is lower alkyl especially methyl.

The patents are hereby incorporated by reference. However neither of these patents describe the use of these compounds as specific analgesics for the treatment of acute and chronic pain, especially rheumatic inflammatory pain. Particularly the antinociceptive profile and properties of this class of compounds are not disclosed.

SUMMARY OF THE INVENTION

Accordingly, the present invention relates to the novel use of a compound having Formula (I) and/or Formula (II) showing antinociceptive properties for treating different types and symptoms of acute and chronic pain, especially non neuropathic inflammatory pain.

Particularly the present invention concerns the use of said compounds of Formulae (I) and/or (II) for the preparation of a pharmaceutical composition for the treatment of different types and symptoms of acute and chronic pain, especially non neuropathic inflammatory pain. This include chronic inflammatory pain e.g. rheumatoid arthritis pain and/or secondary inflammatory osteoarthritic pain.

A compound according to the invention has the general Formula (I)

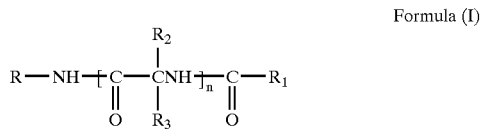

Formula (I)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group, or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, S(O)$_2$, NR$_4$, PR$_4$ or a chemical bond;

Y is hydrogen, lower alkyl, aryl, aryl lower alkyl, lower alkenyl, lower alkynyl, halo, heterocyclic, heterocyclic lower alkyl, lower alkyl, and Y may be unsubstituted or substituted with an electron donating group or an electron withdrawing group, provided that when Y is halo, Z is a chemical bond, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$ or PR$_4$SR$_7$, NR$_4$PR$_5$R$_6$ or PR$_4$NR$_5$R$_7$,

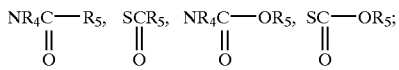

R$_4$, R$_5$ and R$_6$ are independently hydrogen, lower alkyl, aryl, aryl lower alkyl, lower alkenyl, or lower alkynyl, wherein R$_4$, R$_5$ and R$_6$ may be unsubstituted or substituted with an electron withdrawing group or an electron donating group;

R$_7$ is independently R$_6$ or COOR$_8$ or COR$_8$;

R$_8$ is hydrogen or lower alkyl, or aryl lower alkyl, and the aryl or alkyl group may be unsubstituted or substituted with an electron withdrawing group or an electron donating group; and n is 1–4; and a is 1–3.

Furthermore a compound according to the invention has the general Formula (II)

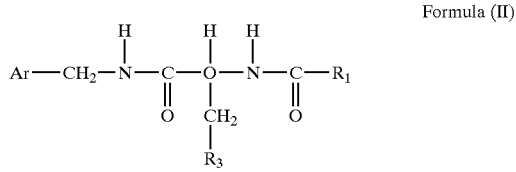

Formula (II)

wherein

Ar is aryl which is unsubstituted or substituted with halo; R$_3$ is lower alkoxy; and R$_1$ is lower alkyl, especially methyl.

The present invention is also directed to the preparation of pharmaceutical compositions comprising a compound according to Formula (I) and/or Formula (II) useful for the treatment of rheumatic inflammatory pain.

DETAILED DESCRIPTION OF THE INVENTION

As indicated hereinabove, the compounds of Formula I are useful for treating pain, particularly non neuropathic inflammatory pain. This type of pain includes chronic inflammatory pain e.g. rheumatoid arthritis pain and/or secondary inflammatory osteoarthritic pain. They show an anti-nociceptive effectiveness.

These compounds are described in U.S. Pat. No. 5,378,729, the contents of which are incorporated by reference.

As defined herein, the "alkyl" groups when used alone or in combination with other groups, are lower alkyl containing from 1 to 6 carbon atoms and may be straight chain or branched. These groups include methyl, ethyl, propyl, isopropyl, butyl, isobutyl, tertiary butyl, amyl, hexyl, and the like.

The "aryl lower alkyl" groups include, for example, benzyl, phenethyl, phenpropyl, phenisopropyl, phenbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10–18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocyenyl. "Lower alkenyl" is an alkenyl group containing from 2 to 6 carbon atoms and at least one double bond.

These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term lower "alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term lower "cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp.16–18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, trifluoromethyl, aryl lower aklyanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl.

As employed herein, the heterocyclic substituent contains at least one sulfur, nitrogen or oxygen ring atom, but also may include one or several of said atoms in the ring. The heterocyclic substituents contemplated by the present invention include heteroaromatics and saturated and partially saturated heterocyclic compounds. These heterocyclics may be monocyclic, bicyclic, tricyclic or polycyclic and are fused rings. They may contain up to 18 ring atoms and up to a total of 17 ring carbon atoms and a total of up to 25 carbon atoms. The heterocyclics are also intended to include the so-called benzoheterocyclics. Representative heterocyclicx include furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the nitric oxides of pyridyl, pyrazinyl, and pyrimidinyl and the like. The preferred heterocyclic are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di, tri and tetrapeptides are also contemplated to be within the scope of the claims.

The preferred values of R is aryl lower alkyl, especially benzyl especially those wherein the phenyl ring thereof is unsubstituted or substituted with electron donating groups or electron withdrawing groups, such as halo (e.g., F).

The preferred $R_1$ is H or lower alkyl. The most preferred $R_1$ group is methyl.

The most preferred electron donating substituents and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. These preferred substituents may be substituted on any one of $R_1$, $R_2$, $R_3$, $R_4$, $R_5$ or $R_6$, $R_7$ or $R_8$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl], and o-hydroxylamino (—O—NH$_2$); alkylamido such as acetamido; trifluoroacetamido; lower alkoxyamino, (e.g., NH(OCH$_3$); and heterocyclicamino, such as pyrazoylamino.

The preferred heterocyclic groups representative of $R_2$ and $R_3$ are monocyclic heterocyclic moieties the formula:

XI

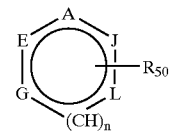

or those corresponding partially or fully saturated form thereof wherein n is 0 or 1; and $R_{50}$ is H or an electron withdrawing group or electron donating group;

A, Z, L and J are independently CH, or a heteroatom selected from the group consisting of N, O, S; and G is CH, or a heteroatom selected from the group consisting of N, O and S, but when n is O, G is CH, or a heteroatom selected from the group consisting of NH, O and S with the proviso that at most two of A, E, L, J and G are heteroatoms.

When n is O, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is O, $R_2$ or $R_3$ may additionally be bonded to the main chain by a nitrogen ring atom.

Other preferred moieties of $R_2$ and $R_3$ are hydrogen, aryl, e.g., phenyl, aryl alkyl, e.g., benzyl and alkyl.

It is to be understood that the preferred groups of $R_2$ and $R_3$ may be unsubstituted or substituted with electron donating or electron withdrawing groups. It is preferred that $R_2$ and $R_3$ are independently hydrogen, lower alkyl, which is either unsubstituted or substituted with an electron withdrawing group or an electron donating group, such as lower alkoxy (e.g., methoxy, ethoxy, and the like), N-hydroxylamino, N-lower alkylhydroxyamino, N-loweralkyl-O-loweralkyl and alkylhydroxyamino.

It is even more preferred that one of $R_2$ and $R_3$ is hydrogen.

It is preferred that n is one.

It is preferred that $R_2$ is hydrogen and $R_3$ is hydrogen, an alkyl group which is unsubstituted or substituted by at least an electron donating or electron withdrawing group or ZY. In this preferred embodiment, it is more preferred that $R_3$ is hydrogen, an alkyl group such as methyl, which is unsubstituted or substituted by an electron donating group, or NR$_4$OR$_5$ or ONR$_4$R$_7$, wherein R$_4$, R$_5$ and R$_7$ are independently hydrogen or lower alkyl. It is preferred that the electron donating group is lower alkoxy, and especially methoxy or ethoxy.

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred $R_1$ is loweralkyl, especially methyl.

The more preferred compounds are compounds of Formula (I) wherein n is 1; $R_2$ is hydrogen; $R_3$ is hydrogen, an alkyl group, especially methyl which is substituted by an electron donating or electron withdrawing group or ZY; R is aryl, aryl lower alkyl, such as benzyl, wherein the aryl group is unsubstituted or substituted and $R_1$ is lower alkyl. In this embodiment, it is most preferred that $R_3$ is hydrogen, an alkyl group, especially methyl, substituted by electron donating group, such as lower alkoxy, (e.g., methoxy, ethoxy and the like), $NR_4OR_5$ or $ONR_4R_7$ wherein these groups are defined hereinabove.

The most preferred compounds utilized are those of the Formula (II):

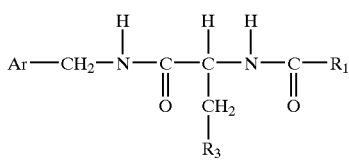

Formula (II)

wherein

Ar is aryl, especially phenyl, which is unsubstituted or substituted with at least one electron donating group or electron withdrawing group, $R_1$ is lower alkyl; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$—Q, wherein Q is lower alkoxy, $NR_4OR_5$ or $ONR_4R_7$ wherein $R_4$ is hydrogen or alkyl containing 1–3 carbon atoms, $R_5$ is hydrogen or alkyl containing 1–3 carbon atoms, and $R_7$ is hydrogen or alkyl containing 1–3 carbon atoms.

The preferred $R_1$ is $CH_3$. The most preferred $R_3$ is methoxy.

The most preferred aryl is phenyl.

The most preferred compound includes:
(R)-2-acetamido-N-benzyl-3-methoxy-propionamide,
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and premutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one (1) or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

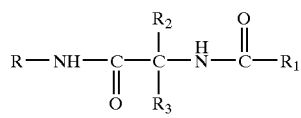

wherein R, $R_1$, $R_2$, $R_3$, $R_4$, $R_5$, $R_6$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

Depending upon the substituents, the present compounds may form addition salts as well. All of these forms are contemplated to be within the scope of this invention including mixtures of the stereoisomeric forms The preparation of the utilized compounds are described in U.S. Pat. Nos. 5,378,729 and 5,773.475, the contents of both of which are incorporated by reference.

The compounds utilized in the present invention are useful as such as depicted in the Formula I or can be employed in the form of salts in view of its basic nature by the presence of the free amino group. Thus, the compounds of Formula I forms salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. It will generally to found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds utilized are administered in amounts ranging from about 1 mg to about 100 mg per kilogram of body weight per day. This dosage regimen may be adjusted by the physician to provide the optimum therapeutic response. For example, several divided doses may be administered daily or the dose may be proportionally reduced as indicated by the exigencies of the therapeutic situation. The compounds of Formula I may be administered in a convenient manner, such as by oral, intravenous (where water soluble), intramuscular or subcutaneous routes.

The compounds of Formula (I) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formula I may be incorporated with excipients and used in the form of ingestible tablets, buccal tablets, troches, capsules, elixirs, suspensions, syrups, wafers, and the like. Such compositions and preparations should contain at least 1% of active compound of Formula I. The percentage of the compositions and preparations may, of course, be varied and may conveniently be between about 5 to about 80% of the weight of the unit. The amount of active compound of Formula I in such therapeutically useful compositions is such that a suitable dosage will be obtained. Preferred compositions or preparations according to the present invention contains between about 10 mg and 6 g active compound of Formula I.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is humans.

The term "treat" refers to either relieving the pain associated with a disease or condition or alleviating the patient's disease or condition.

are assessed and spinal/supraspinal plasticity of nociception is considered as a molecular basis for neuropathic pain particularly during the second (=late) phase of the test, during which most clinically used drugs against neuropathic pain are active. These features have resulted in the formalin test being accepted as a valid model of persistent clinical pain.

The compound was tested for anti-nociceptive properties by use of the weighted behavioural scoring method: Freely moving animals underwent observational assessment of the position of the left hind paw according to a rating score scaled 0–3 before and 10, 20, 30 and 40 min after injection of 0.05 ml of sterile 2.5% formalin under the skin on the dorsal surface of the paw. SPM 927, administered i.p. just prior to formalin injection produced dose dependant reduction of the formalin-induced tonic inflammatory nociceptive behaviour as shown in table 1 (weighted pain scores±SEM, n=11–12/group).

TABLE 1

Weighted pain score, formalin test, rat

| Dose [mg/kg] | No. of Animals | BASELINE | Time After Injection of formalin and SPM 927 | | | |
|---|---|---|---|---|---|---|
| | | | 10 MIN | 20 MIN | 30 MIN | 40 MIN |
| 0 | 11 | 0.00 ± 0.00 | 0.30 ± 0.16 | 0.93 ± 0.21 | 1.84 ± 0.19 | 2.10 ± 0.24 |
| 5 | 12 | 0.01 ± 0.01 | 0.31 ± 0.11 | 0.78 ± 0.23 | 1.47 ± 0.20 | 1.46 ± 0.19* |
| 10 | 11 | 0.00 ± 0.00 | 0.42 ± 0.17 | 0.33 ± 0.16* | 1.02 ± 0.27* | 1.05 ± 0.19* |
| 20 | 12 | 0.00 ± 0.00 | 0.48 ± 0.18 | 0.57 ± 0.14 | 0.78 ± 0.18* | 1.02 ± 0.24* |
| 40 | 12 | 0.00 ± 0.00 | 0.12 ± 0.05 | 0.10 ± 0.04* | 0.09 ± 0.06* | 0.12 ± 0.06* |

*= Significant difference from vehicle (ANOVA corrected for multiple comparisons $p \leq 0.05$.

The compounds of the present invention are useful for treating chronic pain. As used herein, the term "chronic pain" is defined as pain persisting for an extended period of time, for example, greater than three to six months, although the characteristic signs described hereinbelow can occur earlier or later than this period. Vegetative signs, such as lassitude, sleep disturbances, decreased appetite, lose of taste or food, weight loss, diminished libido and constipation develop.

Types of pain that the compounds of the present invention are especially useful in treating are is acute and chronic pain, particularly non neuropathic inflammatory pain. This include chronic inflammatory pain, e.g. rheumatoid arthritis pain and/or secondary inflammatory osteoarthritic pain.

The compounds of the present invention are administered to a patient suffering from the aforementioned type of pain in an analgesic effective amount. These amounts are equivalent to the therapeutically effective amounts described hereinabove.

The following working examples show the antinociceptive properties in well-defined animal models of acute and chronic pain.

The used substance was SPM 927 which is the synonym for Harkoseride. The standard chemical nomenclature is (R)-2-acetamide-N-benzyl-3-methoxypropionamide.

1. EXAMPLE 1

Formalin Test, Rat
Prolonged Inflammatory Pain

Significant and dose dependent efficacy of SPM 927 could be demonstrated in the late phase of the rat formalin test.

The formalin test is a chemically-induced tonic pain model in which biphasic changes of nociceptive behaviour The term ANOVA stands for Analysis of Variance.

2. EXAMPLE 2

Chronic Constriction Injury (CCI, Bennett-Model)

The effectiveness of SPM 927 in reducing spontaneous chronic pain, mechanical allodynia, and thermal hyperalgesia was tested using the chronic constriction injury (CCI) model of peripheral neuropathy, one of the best characterised in vivo animal models used to study chronic pain due to peripheral nerve injury. In this model, loose ligatures are placed around the sciatic nerve, which produces axonal swelling and a partial deafferentation manifested as a significant but incomplete loss of axons in the distal portion of the peripheral nerve. One of the prominent behaviours seen following sciatic nerve ligation is the appearance of hind paw guarding, thought to be an indication of an ongoing spontaneous chronic pain. Support for this idea is derived from reports of increased spinal cord neural activity, and increased spontaneous neuronal discharge in spinothalamic tract neurons and in the ventrobasal thalamus in the absence of overt peripheral stimulation. In addition to the appearance of spontaneous pain behaviours, several abnormalities in stimulus evoked pain occur as a result of CCI, including thermal hyperalgesia and mechanical allodynia. The development of these abnormal stimulus-evoked pains has also been reported as occurring in areas outside the territory of the damaged nerve, areas innervated by uninjured nerves.

Behavioural tests for thermal hyperalgesia, and mechanical allodynia were conducted to evaluate different components of neuropathic pain. Baseline data for each test was collected prior to any experimental procedure; in addition, all animals were tested for the development of chronic pain behaviours 13–25 days after CCI surgery 1 day prior to the day of vehicle (0.04 ml sterile water/10 g body weight) or drug administration and after vehicle/drug administration.

The sequence of the tests was pain-related behaviour (1) thermal hyperalgesia, (2) mechanical allodynia in order to minimise the influence of one test on the result of the next. The testing procedures and results are presented separately for each aspect of chronic pain. Either 0 (vehicle, 0.04 ml/10 g body weight), 5, 10, 20 or 40 mg/kg of SPM 927 (n=7–23/group) was administered i.p. 15 minutes before the first behavioural test.

(1) Thermal hyperalgesia was assessed by means of withdrawal latency in response to radiant heat applied to the subplantar surface of the ligated rat hind paw according to Hargreaves. As compared to the baseline latency (s), a significant decrease in the (postoperative) latency of foot withdrawal in response to the thermal stimulus was interpreted as indicating the presence of thermal hyperalgesia following chronic constriction injury.

SPM 927 dose dependently reduced chronic constriction injury-induced thermal hyperalgesia as shown in table 2 [latencies (s)±SEM]. Significant effects were observed only at the highest doses tested (20 and 40 mg/kg i.p.) with the maximum effect seen already at 20 mg/kg i.p.

TABLE 2

Thermal hyperalgesia, CCI model, rat

| Dose [mg/kg] | No. of Animals | Baseline | Post-operative | Post-operative + SPM 927 |
|---|---|---|---|---|
| 0 | 13 | 9.7 ± 0.73 | 6.9 ± 0.28 | 7.3 ± 0.42 |
| 5 | 7 | 10.5 ± 0.68 | 8.1 ± 0.59 | 9.1 ± 0.97 |
| 10 | 7 | 9.2 ± 0.68 | 7.0 ± 0.60 | 8.0 ± 0.58 |
| 20 | 8 | 9.9 ± 0.69 | 6.9 ± 0.56 | 9.7 ± 0.95* |
| 40 | 8 | 8.3 ± 0.57 | 7.4 ± 0.47 | 10.2 ± 0.77* |

*= Significant difference from vehicle (ANOVA corrected for multiple comparisons p ≦ 0.05).

Mechanical sensitivity and allodynia of the ligated rat hind paw was quantified by brisk foot withdrawal in response to normally innocuous mechanical stimuli as described previously. Responsiveness to mechanical stimuli was tested with a calibrated electronic Von Frey pressure algometer connected to an online computerised data collection system. A significant decrease in the post operative compared to baseline pressure (g/mm$^2$) necessary to elicit a brisk foot withdrawal in response to this mechanical stimulus is interpreted as mechanical allodynia.

(2) SPM 927 dose dependently reduced the intensity of mechanical allodynia induced by unilateral nerve ligation as shown in table 3 [pressure (g/mm$^2$)±SEM]. Regression analysis showed a positive linear correlation between the dose of SPM 927 and the increase in the amount of force required to produce foot withdrawal.

TABLE 3

Mechanical allodynia, CCI model, rat

| Dose [mg/kg] | No. of Animals | Baseline | Post-operative | Post-operative + SPM 927 |
|---|---|---|---|---|
| 0 | 20 | 41.6 ± 2.20 | 18.7 ± 2.08 | 20.2 ± 1.89 |
| 5 | 11 | 53.6 ± 3.34 | 16.4 ± 2.56 | 21.8 ± 2.33 |
| 10 | 17 | 42.9 ± 2.54 | 21.1 ± 2.12 | 29.2 ± 2.84* |
| 20 | 8 | 46.0 ± 2.62 | 24.6 ± 2.78 | 39.5 ± 3.62* |
| 40 | 9 | 48.3 ± 3.83 | 23.8 ± 2.23 | 42.9 ± 5.47* |

*= Significant difference from vehicle (ANOVA corrected for multiple comparisons, p ≦ 0.05).

3. EXAMPLE 3

Randall-Selitto Paw Pressure Test, Rat

Further potential anti-nociceptive efficacy of SPM 927 was assessed in a rat experimental model of acute inflammation using a modified Randall and Selitto. procedure. Acute inflammation is induced by injection of s.c. carrageenen (1.0 mg in 0.1 ml saline/paw), an unspecific inflammatory agent, into the plantar surface of one hind paw of the animal. Mechanical sensitivity and nociceptive thresholds were measured using an algesimeter device that exerts a constantly increasing mechanical force (10 mm Hg/sec) on the inflammed hind paw. The mechanical nociceptive threshold is defined as the pressure (mm Hg) at which the rat vocalises or struggles or withdraws its paw. Since its original description, the Randall and Selitto mechanical paw pressure test has become a standard method for testing the efficacy of new compounds for alleviating acute inflammatory pain.

SPM 927 or vehicle (sterile water, 0.04 ml/log body weight) was administered i.p 1 hr and 45 minutes after carrageenen, meaning 15 to 20 minutes before the start of behavioural testing. As compared to the response threshold of vehicle-treated controls, an increase in the pressure required to produce a behavioural response is interpreted as antinociception. SPM 927 at 20 and 40 mg/kg i.p. significantly increased the pressure required to elicit a paw withdrawal during acute carrageenen induced inflammation in the Randall-Sellito paw pressure test, indicating a reduction of mechanical hyeralgesia as shown in table 4 [pressure (mm Hg)±SEM, n=12/group].

TABLE 4

Mechanical hyperalgesia, modified Randall-Selitto, rat

| Dose [mg/kg] | Baseline | Carrageenen alone | Carrageenen + SPM 927 |
|---|---|---|---|
| 0 | 101.5238 ± 14,9666 | 40.85714 ± 9,319 | 45.07143 ± 5,569 |
| 20 | 142.5694 ± 12.834 | 108.222 ± 10.180 | 164.7639 ± 13.533* |
| 40 | 164.8889 ± 18.360 | 89.963 ± 7.457 | 232.741 ± 22.034*. |

*= Significant difference from vehicle (ANOVA corrected for multiple comparisons, p ≦ 0.05).

Due to high variation of baseline responses and mechanical hyperalgesia following carrageenen injection, a direct comparison of the absolute paw pressures required to elicit a behavioural response is inappropriate. However, vehicle (0 mg /kg, sterile water, 0.04 ml/10 g body weight) had little effect on behavioural responsiveness, but SPM 927 at doses of 20 and 40 mg/kg i.p. markedly reduced the mechanical hyperalgesia induced by carrageenen.

Test Results

Harkoseride proved to be anti-nociceptive in several different experimental animal models that reflect different types and symptoms of pain. The prolonged inflammatory nociception produced in the rat formalin test and mechanical allodynia in the rat CCI model appeared most sensitive to the effects of SPM 927, showing significant dose dependent reductions in nociceptive behaviour measurements, even at the 10 mg/kg i.p. dose. In addition, but at higher doses SPM 927 exhibited statistically significant reduction in pain on other types of nociception, thermal hyperalgesia (paw flick Hargreaves test, rat CCI model), and mechanical hyperalgesia due to acute inflammation (modified rat Randall-Selitto test).

Thus, the anti-nociceptive profile of SPM 927 differs from classical analgesics like opioids and the standard anti-inflammatory drugs of the NSAID-type (non-steroidal anti-inflammatory drug), furthermore and surprisingly, the antinociceptive profiling obtained and described by the data given table 1–4 is even different to other anticonvulsant drugs used for pain relief.

The weak but not significant effects on thermal and mechanical hyperalgesia led to the following investigation:

4. EXAMPLE 4

Antinociceptive Effects of Harkoseride in an Animal Model for Rheumatoid Arthritis In the following study harkoseride is hereinafter referred to as SPM 927.

Method:

Experiments were performed in female Wistar rats weighing 80–90 g at the beginning of the experiments. Arthritis was induced by intraplantar injection of Freund's complete adjuvans (FCA, 0.1 ml) to one hindpaw. Drugs were given on day 11 after FCA injection in animals which developed systemic secondary arthritic symptoms as assessed by visual inspection. Mechanical hyperalgesia was than acutely applied and measured by means of the paw pressure test (Randall Selitto method) and supraspinal vocalisation as the biological endpoint of the nociceptive reaction. Measurements were taken at 0 min (before drug injection) and 15 min, 30 min, 60 min, and 24 h after drug injection and all data are expressed as percent of maximal possible effect (% MPE).

10 groups of 15 rats were used and received the following treatments:

| No. | FCA | drug [dose in mg/kg]/time | comment |
|---|---|---|---|
| 1 | no | no | healthy controls |
| 2 | yes | no | arthritic controls |
| 3 | yes | SPM 927 [5] acute | treatment group (anti-nociceptive effects) |
| 4 | yes | SPM 927 [10] acute | treatment group (anti-nociceptive effects) |
| 5 | yes | SPM 927 [20] acute | treatment group (anti-nociceptive effects) |
| 6 | yes | SPM 927 [30] acute | treatment group (anti-nociceptive effects |
| 7 | yes | SPM 927 [40] acute | treatment group (anti-nociceptive effects) |
| 8 | yes | SPM 927 [30] early (with FCA) | treatment group (anti-inflammatory effects) |
| 9 | no | morphine [10] | positive control group (normal condition) |
| 10 | yes | morphine [10] | positive control group (disease condition) |

Results:

| | | % MPE | | | |
|---|---|---|---|---|---|
| group # | treatment | 15 min | 30 min | 60 min | 24 h |
| 1 | Control | −5 | −2 | +2 | −5 |
| 2 | FCA/VEH | +12 | +2 | 0 | +3 |
| 3 | FCA/SPM 5 | −5 | −5 | −12 | −14 |
| 4 | FCA/SPM 10 | +7 | −2 | 0 | −5 |
| 5 | FCA/SPM 20 | +1 | −20 | −9 | −20 |
| 6 | FCA/SPM 30 | +58 | +33 | +16 | −8 |
| 7 | FCA/SPM 40 | +100 | +100 | +14 | −7 |
| 8 | FCA/SPM 30 (early) | −14 | −7 | −3 | −11 |

-continued

| | | % MPE | | | |
|---|---|---|---|---|---|
| group # | treatment | 15 min | 30 min | 60 min | 24 h |
| 9 | MOR 10 | +100 | +100 | +100 | +2 |
| 10 | FCA/MOR10 | +100 | +100 | +100 | −7 |

SPM 927 showed dose-dependent anti-nociceptive but no anti-inflammatory effects. The anti-nociceptive effects started at a dose of 30 mg/kg and were most prominent during the first 30 min of testing. Morphine, as a positive control substance had clear antinociceptive effects in arthritic and normal animals.

Conclusion:

Surprisingly and unexpected SPM 927 shows dose-dependent antinociceptive effects in rats that suffer from Freund's complete adjuvans induced arthritis (significant so at doses of 30 and 40 mg/kg). This antinociception is not caused by potential anti-inflammatory effects. Under this chronic inflammatory pain condition the antinociceptive effect of SPM 927 (see FIG. 1) showed full intrinsic activity and suggests SPM 927 to be effective in rheumatoid arthritic pain as well as secondary inflammatory osteoarthritis.

What is claimed is:

1. A method of treating a mammal suffering from or susceptible to acute or chronic pain, comprising administering to the mammal an effective amount of a compound of the following Formula (I):

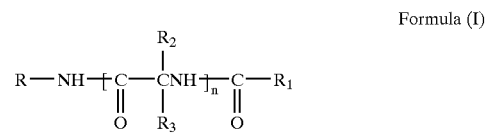

Formula (I)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; $R_2$ and $R_3$ are independently hydrogen, lower alkyl, lower alkenyl, lower alkynyl, aryl lower alkyl, halo, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group; and wherein heterocyclic in $R_2$ and $R_3$ is furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl morpholinyl, benzoxazolyl, tetrahydrofuryl, pyranyl, indazolyl, purinyl, indolinyl, pyrazolindinyl, imidazolinyl, imidazolindinyl, pyrrolidinyl, furazanyl, N-methylindolyl, methylfuryl, pyridazinyl, pyrimidinyl, pyrazinyl, epoxy, aziridino, oxetanyl or azetidinyl;

Z is O, S, S(O)$_2$, NR$_6'$; or PR$_4$;

Y is hydrogen, lower alkyl, aryl, aryl lower alkyl, lower alkenyl, lower alkynyl, heterocyclic, heterocyclic lower alkyl, and Y may be unsubstituted or substituted with an electron donating group or an electron withdrawing group, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$, PR$_4$SR$_7$, NR$_4$PR$_5$R$_6$ or PR$_4$NR$_5$R$_7$.

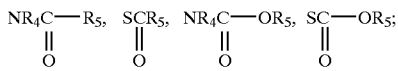

R$_6'$ is hydrogen, lower alkyl, lower alkenyl, or lower alkynyl and R$_4$ may be unsubstituted or substituted with an electron withdrawing group or electron donating group;

R$_4$, R$_5$ and R$_6$ are independently hydrogen, lower alkyl, aryl, aryl lower alkyl, lower alkenyl, or lower alkynyl, wherein R$_4$, R$_5$ and R$_6$ may be unsubstituted or substituted with an electron withdrawing group or an electron donating group; and R$_7$, is COOR$_8$, COR$_8$, hydrogen, lower alkyl, aryl, aryl lower alkyl, lower alkenyl or lower alkynyl, which R$_7$ may be unsubstituted or substituted with an electron withdrawing group or an electron donating group;

R$_8$ is hydrogen or lower alkyl, or aryl lower alkyl, and the aryl or alkyl group may be unsubstituted or substituted with an electron withdrawing group or an electron donating group; and n is 1–4; and a is 1–3, or a pharmaceutically acceptable salt thereof.

2. The method of claim 1 wherein one of R$_2$ and R$_3$ is hydrogen.

3. The method of claim 1 wherein n is 1.

4. The method of claim 1 wherein one of R$_2$ and R$_3$ is hydrogen and n is 1.

5. The method of claim 1 wherein R is aryl lower alkyl and R$_1$ is lower alkyl.

6. The method of claim 1 wherein R$_2$ and R$_3$ are independently hydrogen, lower alkyl, or ZY;

Z is O, NR$_4$ or PR$_4$;

Y is hydrogen or lower alkyl or

ZY is NR$_5$R$_6$R$_7$, NR$_5$OR$_6$, ONR$_5$R$_7$,

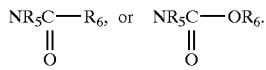

7. The method of claim 4 wherein R$_2$ and R$_3$ are independently hydrogen, lower alkyl, or ZY;

Z is O, NR$_4$ or PR$_4$;

Y is hydrogen or lower alkyl;

ZY is NR$_5$R$_6$R$_7$, NR$_5$OR$_6$, ONR$_5$R$_7$,

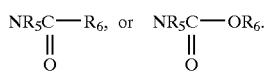

8. The method of claim 4 wherein R$_2$ is hydrogen and R$_3$ is lower alkyl, which may be substituted or unsubstituted with an electron donating or electron withdrawing group, NR$_4$OR$_5$, or ONR$_4$R$_7$.

9. The method of claim 4 wherein R$_3$ is lower alkyl which is unsubstituted or substituted with hydroxy or loweralkoxy, NR$_4$OR$_6$ or ONR$_4$R$_7$, wherein R$_5$ and R$_7$, are independently hydrogen or lower alkyl, R is aryl lower alkyl, which aryl group may be unsubstituted or substituted with an electron withdrawing group and R$_1$ is lower alkyl.

10. The method of claim 9 wherein aryl is phenyl.

11. The method of claim 9 wherein aryl is phenyl and is unsubstituted or substituted with halo.

12. The method of claim 1 wherein the compound is:

(R)-2-acetamide-N-benzyl-3-methoxy-propionamide;

O-methyl-N-acetyl-D-serine-m-fluorobenzylamide;

O-methyl-N-acetyl-D-serine-p-fluorobenzylamide;

N-acetyl-D-phenylglycinebenzylamide;

D-1,2-(N, O-dimethylhydroxylamino)-2-acetamide acetic acid benzylamide; or

D-1,2-(O-methylhydroxylamino)-2-acetamido acetic acid benzylamide; or a pharmaceutically acceptable salt thereof.

13. The method of claim 1 wherein the mammal is suffering from non neuropathic inflammatory pain.

14. The method of claim 9 wherein the mammal is suffering from non neuropathic inflammatory pain.

15. The method of claim 1 wherein the mammal is suffering from acute pain.

16. The method of claim 1 wherein the mammal is suffering from chronic pain.

17. The method of claim 1 wherein the mammal is suffering from chronic inflammatory pain.

18. The method of claim 1 wherein the mammal is suffering from rheumatoid arthritis pain.

19. The method of claim 1 wherein the mammal is suffering from secondary inflammatory osteoarthritic pain.

20. The method of claim 1 wherein the mammal pain is not nociceptive pain.

21. A method of treating a mammal suffering from or susceptible to acute or chronic pain, comprising administering to the mammal an effective amount of a compound of the following Formula (II)

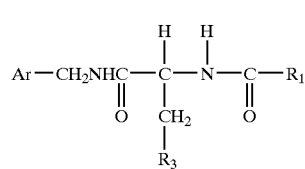

Formula (II)

wherein

Ar is phenyl which is unsubstituted or substituted with at least one halo group;

R$_3$ is lower alkoxy containing 1–3 carbon atoms and R$_1$ is lower alkyl containing 1–3 carbon atoms or a pharmaceutically acceptable salt thereof.

22. The method of claim 21 wherein the mammal is suffering from non neuropathic inflammatory pain.

23. The method of claim 22 wherein Ar is unsubstituted phenyl.

24. The method of claim 21 or 22 wherein halo is fluoro.

25. The method of claim 21 or 23 wherein R$_3$ is alkoxy containing 1–3 carbon atoms and Ar is unsubstituted phenyl.

26. A method of treating a mammal suffering from or susceptible to non neuropathic inflammatory pain, comprising administering to the mammal an effective amount of a compound in the R configuration having the formula

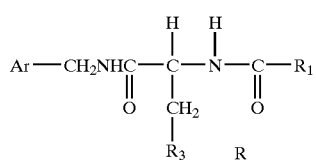

wherein

Ar is phenyl which is unsubstituted or substituted with at least one halo group; R₃ is lower alkoxy containing 1–3 carbon atoms and R₁ is methyl, or of a pharmaceutically acceptable salt thereof.

27. The method of claim 26 wherein the compound is substantially enantiopure.

28. The method of claim 26 or 27 wherein Ar is unsubstituted phenyl.

29. The method of claim 26 or 27 wherein halo is fluoro.

30. The method of claim 26 or 27 wherein R₃ is alkoxy containing 1–3 carbon atoms and Ar is unsubstituted phenyl.

31. A method of treating a mammal suffering from or susceptible to non neuropathic inflammatory pain, comprising administering to the mammal an effective amount of (R)-2-Acetamide-N-benzyl-3-methoxy propionamide or a pharmaceutically acceptable salt thereof.

32. A method of treating a mammal suffering from or susceptible to chronic inflammatory pain, comprising administering to the mammal an effective amount of (R)-2-Acetamide-N-benzyl-3-methoxy-propionamide or its pharmaceutically acceptable salt thereof.

33. The method of claim 32 wherein the mammal is suffering from pain associated with rheumatoid arthritis.

34. The method of claim 32 wherein the mammal is suffering from secondary inflammatory osteoarthritic pain.

35. The method of any one of claims 31 through 34 wherein the compound is substantially enantiopure.

36. A pharmaceutical composition comprising a pharmaceutical carrier and a non neuropathic-inflammatory pain effective amount of a compound of the following Formula (I):

Formula (I)

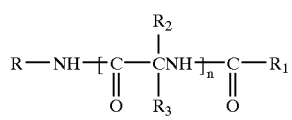

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

R₁ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; R₂ and R₃ are independently hydrogen, lower alkyl, lower alkenyl, lower alkynyl, aryl lower alkyl, halo, heterocyclic, heterocyclic lower alkyl, lower alkyl heterocyclic, lower cycloalkyl, lower cycloalkyl lower alkyl, or Z-Y wherein R₂ and R₃ may be unsubstituted or substituted with at least one electron withdrawing group or electron donating group; and wherein heterocyclic in R₂ and R₃ is furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imidazolindinyl, pyrrolidinyl, furazanyl, N-methylindolyl, methylfuryl, pyridazinyl, pyrimidinyl, pyrazinyl, epoxy, aziridino, oxetanyl or azetidinyl;

Z is O, S, S(O)₂, NR₆'; or PR₄;

Y is hydrogen, lower alkyl, aryl, aryl lower alkyl, lower alkenyl, lower alkynyl, heterocyclic, heterocyclic lower alkyl, and Y may be unsubstituted or substituted with an electron donating group or an electron withdrawing group, or ZY taken together is NR₄NR₅R₇, NR₄OR₅, ONR₄R₇, OPR₄R₅, PR₄OR₅, SNR₄R₇, NR₄SR₇, SPR₄R₅, PR₄SR₇, NR₄PR₅R₆ or PR₄NR₅R₇,

R₆' is hydrogen, lower alkyl, lower alkenyl, or lower alkynyl and R₄ may be unsubstituted or substituted with an electron withdrawing group or electron donating group;

R₄, R₅ and R₆ are independently hydrogen, lower alkyl, aryl, aryl lower alkyl, lower alkenyl, or lower alkynyl, wherein R₄, R₅ and R₆ may be unsubstituted or substituted with an electron withdrawing group or an electron donating group; and R₇, is COOR₈, COR₃, hydrogen, lower alkyl, aryl, aryl lower alkyl, lower alkenyl or lower alkynyl, which R₇, may be unsubstituted or substituted with an electron withdrawing group or an electron donating group;

R₈ is hydrogen or lower alkyl, or aryl lower alkyl, and the aryl or alkyl group may be unsubstituted or substituted with an electron withdrawing group or an electron donating group; and n is 1–4; and a is 1–3, or a pharmaceutically acceptable salt thereof.

37. The pharmaceutical composition of claim 36 wherein the compound is:

(R)-2-acetamide-N-benzyl-3-methoxy-propionamide;

O-methyl-N-acetyl-D-serine-m-fluorobenzylamide;

O-methyl-N-acetyl-D-serine-p-fluorobenzylamide;

N-acetyl-D-phenylglycinebenzylamide;

D-1,2=(N,O-dimethylhydroxylamino)-2-acetamide acetic acid benzylamide; or

D-1,2-(O-methylhydroxylamino)-2-acetamido acetic acid benzylamide; or a pharmaceutically acceptable salt thereof.

* * * * *

UNITED STATES PATENT AND TRADEMARK OFFICE
CERTIFICATE OF CORRECTION

PATENT NO. : 6,803,481 B2
DATED : October 12, 2004
INVENTOR(S) : Norma Selve

It is certified that error appears in the above-identified patent and that said Letters Patent is hereby corrected as shown below:

Title page,
Item [30], Foreign Application Priority Data, please correct "01106891" to -- 01106891.3 --

Column 1,
Line 10, please correct "neurophathic" to -- neurophathic --

Column 2,
Line 10, please correct " $Ar-CH_2-N-C-O-N-C-R_1$ with O, CH$_2$, O, R$_3$ " to -- $Ar-CH_2-N-C-C-N-C-R_1$ with O, CH$_2$, O, R$_3$ --

Column 3,
Line 33, please correct " $Ar-CH_2-N-C-O-N-C-R_1$ with O, CH$_2$, O, R$_3$ " to -- $Ar-CH_2-N-C-C-N-C-R_1$ with O, CH$_2$, O, R$_3$ --

Column 4,
Line 52, please correct "aklyanoyl" to -- alkyanoyl --

Column 7,
Line 56, please correct "premutations" to -- permutations --

Column 14,
Line 18, please correct "ml/log" to -- ml/10g --
Line 28, please correct "hyeralgesia" to -- hyperalgesia --

Column 16,
Lines 61-62, please correct "benzothienyl morpholinyl," to -- benzothienyl, morpholinyl, --

UNITED STATES PATENT AND TRADEMARK OFFICE
CERTIFICATE OF CORRECTION

PATENT NO. : 6,803,481 B2
DATED : October 12, 2004
INVENTOR(S) : Norma Selve

It is certified that error appears in the above-identified patent and that said Letters Patent is hereby corrected as shown below:

Column 17,
Lines 40-49, please correct
"6. The method of claim 1 wherein $R_2$ and $R_3$ are independently hydrogen, lower alkyl, or ZY;

Z is O, $NR_4$ or $PR_4$;
    Y is hydrogen or lower alkyl or
    ZY is $NR_5R_6R_7$, $NR_5OR_6$, $ONR_5R_7$, $$NR_5\underset{O}{\overset{\|}{C}}-R_6, \text{ or } NR_5\underset{O}{\overset{\|}{C}}-OR_6.$$
" to -- 6. The method of claim 1 wherein $R_2$ and $R_3$ are independently hydrogen, lower alkyl, or ZY;

Z is O, $NR_6$' or $PR_4$;
    Y is hydrogen or lower alkyl or
    ZY is $NR_4NR_5R_7$, $NR_4OR_5$, $ONR_4R_7$, $$NR_4\underset{O}{\overset{\|}{C}}-R_5, \text{ or } NR_4\underset{O}{\overset{\|}{C}}-OR_5.$$ --

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,803,481 B2
DATED : October 12, 2004
INVENTOR(S) : Norma Selve

It is certified that error appears in the above-identified patent and that said Letters Patent is hereby corrected as shown below:

Column 1,
Line 10, please correct "neurophathic" to -- neuropathic --.

Signed and Sealed this

Twentieth Day of September, 2005

JON W. DUDAS
*Director of the United States Patent and Trademark Office*

UNITED STATES PATENT AND TRADEMARK OFFICE
CERTIFICATE OF CORRECTION

PATENT NO.       : 6,803,481 B2                                    Page 1 of 1
APPLICATION NO.  : 10/344885
DATED            : October 12, 2004
INVENTOR(S)      : Norma Selve It is certified that error appears in the above-identified patent and that said Letters Patent is hereby corrected as shown below:

Column 20, Line 40:     "$COR_3$" to --$COR_8$--.

Signed and Sealed this

Sixth Day of November, 2007

JON W. DUDAS
*Director of the United States Patent and Trademark Office*